US00PP33150P3

(12) United States Plant Patent
Hansoti

(10) Patent No.: US PP33,150 P3
(45) Date of Patent: Jun. 8, 2021

(54) ***SANSEVIERIA* PLANT NAMED 'HANSOTI23'**

(50) Latin Name: *Sansevieria trifasciata*
Varietal Denomination: HANSOTI23

(71) Applicant: Ashish Hansoti, Mumbai (IN)

(72) Inventor: Ashish Hansoti, Mumbai (IN)

( * ) Notice: Subject to any disclaimer, the term of this patent is extended or adjusted under 35 U.S.C. 154(b) by 0 days.

(21) Appl. No.: 17/010,550

(22) Filed: Sep. 2, 2020

(65) Prior Publication Data

US 2021/0076550 P1 Mar. 11, 2021

(30) Foreign Application Priority Data

Sep. 10, 2019 (QZ) ..... PBR 2019/2122

(51) Int. Cl.
*A01H 5/12* (2018.01)
*A01H 6/12* (2018.01)

(52) U.S. Cl.
USPC ..... Plt./382
CPC ..... *A01H 6/12* (2018.05)

(58) Field of Classification Search
USPC ..... Plt./382
CPC ..... A01H 6/12; A01H 5/12
See application file for complete search history.

*Primary Examiner* — Keith O. Robinson
(74) *Attorney, Agent, or Firm* — Cassandra Bright

(57) ABSTRACT

A new and distinct cultivar of *Sansevieria* plant named 'HANSOTI23' is disclosed, characterized by bright, variegated foliage of green and cream tones with linear bands along the length of the leaf, contrasting with a base background cream colour and bright green coloured margin bands in the leaf blade. Foliage is arranged in attractive spiral rosettes with lowermost foliage occurring at obtuse angles from the center of the plant. The new cultivar is compact, reaching about 20 to 25 cm in height at maturity. Plants are typically ready to sell at 3 months from a rooted liner, having 9 to 12 leaves at this stage. Plants require little water, having a moderate tolerance for drought, and are also tolerant of very wet conditions. The new variety is a *Sansevieria*, categorized within the Compact *Sansevieria* Group, typically produced as an indoor ornamental plant.

7 Drawing Sheets

Latin name of the genus and species: *Sansevieria trifasciata.*

Variety denomination: 'HANSOTI23'.

BACKGROUND OF THE INVENTION

The present invention relates to a new and distinct cultivar of *Sansevieria* plant, botanically known as *Sansevieria trifasciata*, of the family Asparagaceae, hereinafter referred to by the cultivar name 'HANSOTI23'.

*Sansevieria* is a monocotyledonous plant with fleshy, succulent leaves which are available in a huge range of species, varieties and cultivars as an outdoor ornamental plant (under tropical conditions) or as indoor plants.

Both, the parental 'Midi Green' (unpatented) and the new cultivar 'HANSOTI23' belong to the group of *Sansevieria trifasciata* called 'Compact *Sansevieria* Group' with *Sansevieria trifasciata* 'Futuna Superba' as the typical example, in contrast to the "Birds Nest" or "Hahnii *Sansevieria* Group" of very short or dwarf cultivars all derived from the original *Sansevieria trifasciata* 'Hahnii' (unpatented) and the "Tall *Sansevieria* Group" of *Sansevieria trifasciata* cultivars with tall leaves up to 4 feet (1.25 meters) tall or even more and *Sansevieria trifasciata* 'Laurentii' (unpatented) as the typical example.

The new *Sansevieria* 'HANSOTI23' was discovered and selected by the inventor, Ashish Hansoti, as a single, naturally occurring whole plant mutation within a planting of *Sansevieria trifasciata* 'Midi Green' (unpatented). The discovery was made at the inventor's nursery, in Village Done, District Thane, Maharashtra State in Western India. The inventor noted the individual plant's uniquely variegated foliage. 'HANSOTI23' originated as a naturally-occurring mutation of the *Sansevieria* variety 'Midi Green' (unpatented) selected in January 2000.

Asexual reproduction of the new *Sansevieria* cultivar by vegetative cuttings was first performed in November of 2007 at a commercial nursery in Village Asle, District Satara, Maharashtra State in Western India. This first and subsequent propagation have shown that the distinctive combination of characteristics of the new cultivar are reproduced true to type as long as the propagation was done through side shoots (basal suckers) originating from the base of the originally discovered plant. Thus, it can be said that the new cultivar reproduces true to type through side shoots (basal suckers).

BRIEF SUMMARY OF THE INVENTION

The following traits have been repeatedly observed and are determined to be unique characteristics of 'HANSOTI23', which in combination distinguish this *Sansevieria* as a new and distinct cultivar:

1. Bright variegated foliage of dark green and cream tones with linear bands along the length of the leaf, contrasting with a base background cream colour and bright green coloured margin bands in the leaf blade. The amount of green in the leaf in inversely proportional to the light level, with plants in highest light being the brightest, with darker yellows and lighter greens and so more colourful. Overall 'HANSOTI23' is one of the most colourful *Sansevieria* hybrids known to the inventor.

2. Bright marginal band of 1 to 10 mm wide. Typically, this band is very narrow on one side of the leaf and much broader on the other side of the same leaf but can, in some leaves, be equally wide on both edges.
3. 20-25 cm plant height overall, one of the most compact cultivars amongst the *Sansevieria* nominated as "Compact *Sansevieria* Group".
4. Ready to sell, 3-month (from rooted Liner) old plants have 9 to 12 (average of 10) leaves per plant which is relatively high compared to other *Sansevieria* in the Compact Group. This gives a more bushy, full plant compared to other *Sansevierias* in the Compact Group.
5. Relatively soft leaves with a slight twist along the long axis of the leaf. In comparison, most *Sansevierias* in the Compact Group have very stiff, upright leaves.

The new variety 'HANSOTI23' is considered a variety of *Sansevieria* in the group denominated as "Compact *Sansevieria* Group". The new variety presents an average of 10 leaves per plant when it reaches maturity (between 3-4 months from rooted Liner).

The new variety has an erect growth habit and the entire plant can reach a height range between 20 and 30 cm. The leaves are of medium width (5 to 7 cm measured at the widest part of the mature leaf under good growing conditions) and lanceolate with a firm, waxy texture. The blades are somewhat thick or fleshy but much less than similar Compact Group of *Sansevieria* and very slightly wavy. This variety also has an inverted triangle shape like most *Sansevieria* of the Compact Group.

The new variety is moderately drought tolerant and adapts well to conditions of bright light and heavy shade (exterior and interior).

The leaves show a bright variegated colouration, with vertical central wide band and occasional thin bands on a background of creamy yellow. This creamy colour covers or overlays the central dark band to varying degrees so that this dark band can appear anywhere between a bright green to a lighter greyish green. The amount of cream on a leaf varies. Overall colour also depends on amount of light available as well as age of the plant—under higher shade overall colour is darker green and less yellow; under higher light colour is brighter with darker yellows and lighter and less green, giving a more golden appearance. The base creamy colour varies from 11B to 11D (The former under more shade and latter under more light).

The central broad band shows green colourations varying from a dark green similar to 136B to a lighter colour similar to 138B or 138C. However, due to extreme variability of shade and the overlying grey colouration it is difficult to pin point the exact shade. Attached colour pictures are a better guide to the overall colouration than written descriptions.

Each leaf has a marginal band that is brighter green and is often (but not always) very narrow on one side of the leaf and broader on the other—the band varies in width from just 2 mm to 10 mm. This marginal band, again variable in colour, has little or no grey overlay and so appears brighter. Colour of this marginal band varies from a light green near N144D on younger leaves to a dark green on older leaves near 136A.

Superimposed on all the above are lighter horizontal cross-banding (typical of most broad leaved *Sansevieria* including 'Futura Superba') that is more obvious over darker central and marginal bands and very indistinct across the creamy base colour.

Backside of the leaves is similarly coloured with wide central darker band and thinned marginal bands. However, usually the whole of the backside of the leaf is more uniform due to thicker overlying layer of greenish-cream (Yellow-Green 150D or 154D where the cream is separate) so that the darker vertical bands (136A) are less distinct that on the front or top of the leaf.

Young shoots are obviously much paler with a whitish cream colour similar to but even lighter than 150D on inside of leaf and similar to 148C on the outside and a very pale background colour of 2C. Marginal band is brighter green. In emerging pups, the horizontal banding is prominent especially on the margins. The cream area is also much lighter, almost white but this slowly darkens to cream as the plant matures.

COMMERCIAL COMPARATOR

Plants of the new *Sansevieria* 'HANSOTI23' are horticulturally similar to the commercial variety 'Futura Superba', unpatented. The varieties, however, vary substantially, as described in the characteristics in Table 1. Plants of the new *Sansevieria* 'HANSOTI23' differ from plants of the commercial cultivar 'Futura Superba' (unpatented) in the characteristics described in Table 1.

TABLE 1

Comparison of Closest similar cultivar 'Futura Superba' and New variety 'Hansoti 23'

| | Characteristic | 'Futura Superba' | 'HANSOTI23' |
|---|---|---|---|
| 1. | Overall color | Thin cream colored marginal variegation and moderate central banding | Bright cream with bright green bands of various widths, bright, variegated appearance. |
| 2. | Leaf aspect | Upright and very slightly undulating | Slightly to moderately undulating. |
| 3. | Mature height | 30 to 60 cm | 20 to 30 cm |

PARENTAL COMPARISON

Plants of the new *Sansevieria* 'HANSOTI23' differ from plants of the parental cultivar in the characteristics described in Table 2.

TABLE 2

Comparison of New and Parental variety

| | Characteristic | Parent 'Midi Green' | 'HANSOTI23' |
|---|---|---|---|
| 1. | Overall color | Dark green with prominent horizontal bands and no variegation. | Bright cream with bright green bands of various widths, bright, variegated appearance. |
| 2. | Margin color | No marginal coloration. | Bright green border 1 to 10 mm wide. |
| 3. | Leaf aspect | Flat | Slightly to moderately undulating. |
| 4. | Vigour | Very vigorous. | Less vigorous, but strong grower. |
| 5. | Leaf width | 5 cm | 6 cm |

BRIEF DESCRIPTION OF THE PHOTOGRAPHS

The accompanying photographs illustrate the overall appearance of the new *Sansevieria* cultivar 'HANSOTI23' showing the colors as true as is reasonably possible with colored reproductions of this type. Colors in the photographs may differ slightly from the color value cited in the detailed botanical description which accurately describe the color of 'HANSOTI23'.

These pictures illustrate the plant form which is the unique characteristic of 'HANSOTI23' and at the same time demonstrates that plant coloration and variegation pattern is similar to several other *Sansevieria trifasciata* cultivars. All plants were grown in an open poly house (high tunnel) at Village Asle, District Satara, Maharashtra State in Western India. Average temperature in Asle is 25° C. with summer highs of 39° C. and winter lows of 6° C. Plants grow under natural light conditions and between 30% to 75% shade levels depending on the season (higher shade in hot summer conditions). These conditions closely approximate those used in commercial practice in India.

Figure 3:
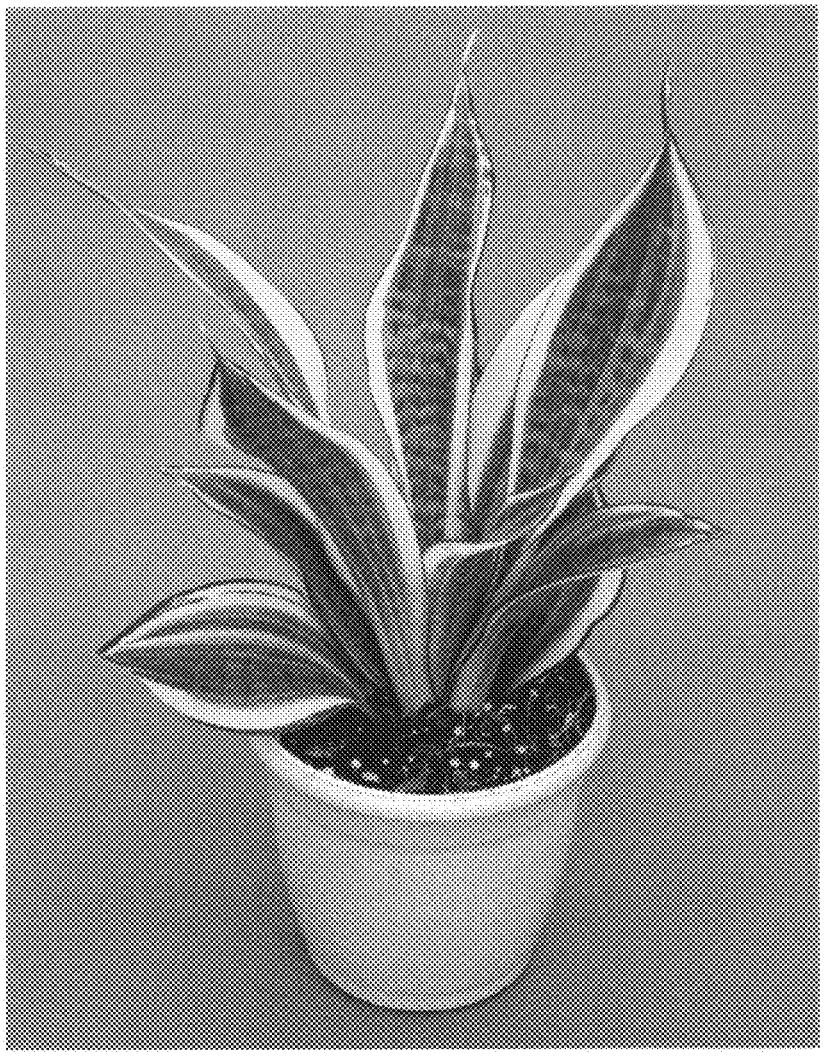

FIG. 3 shows a plant of 'Hansoti23' grown under high light conditions (about 35% shade from the greenhouse plastic and no shade cloth in late spring which is bright and sunny season) showing the bright coloration, with more, darker yellows and narrower and lighter green bands that high light brings. Though more colourful, such high light grown plants are less acclimatised to low light indoor conditions. Age of the plant is approximately 3 months.

Figure 1:
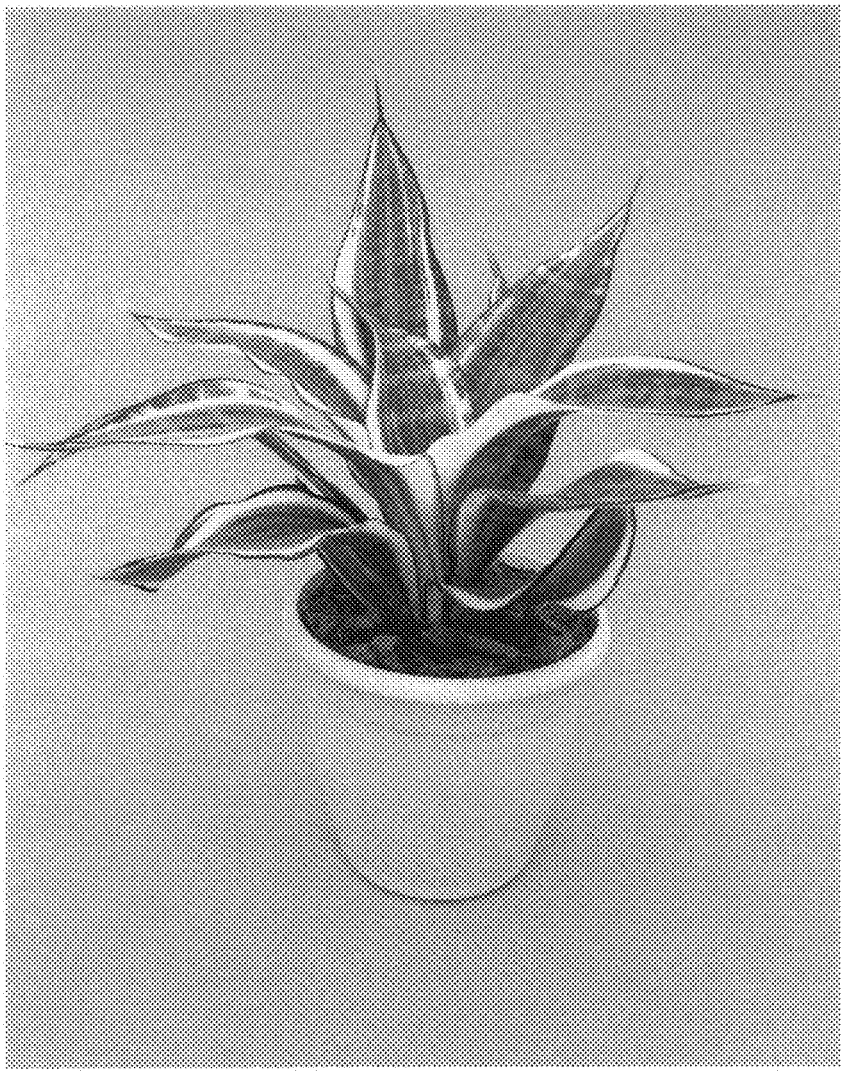
FIG. 1 illustrates a three-month-old plant of *Sansevieria* 'HANSOTI23' in a 12 cm diameter pot.
Figure 2:
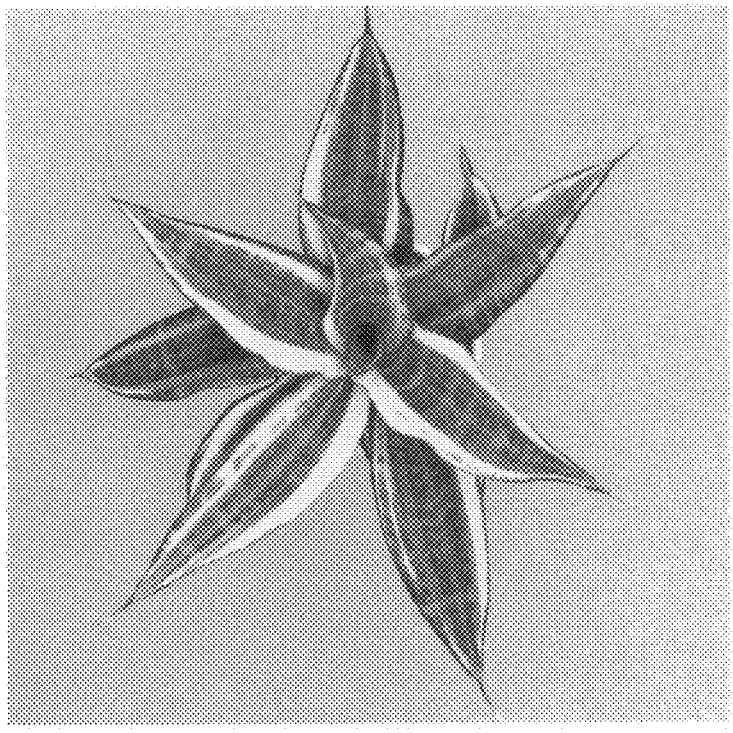
FIG. 2 illustrates a top view of the plant of 'HANSOTI23' in FIG. 1.
Figure 4:
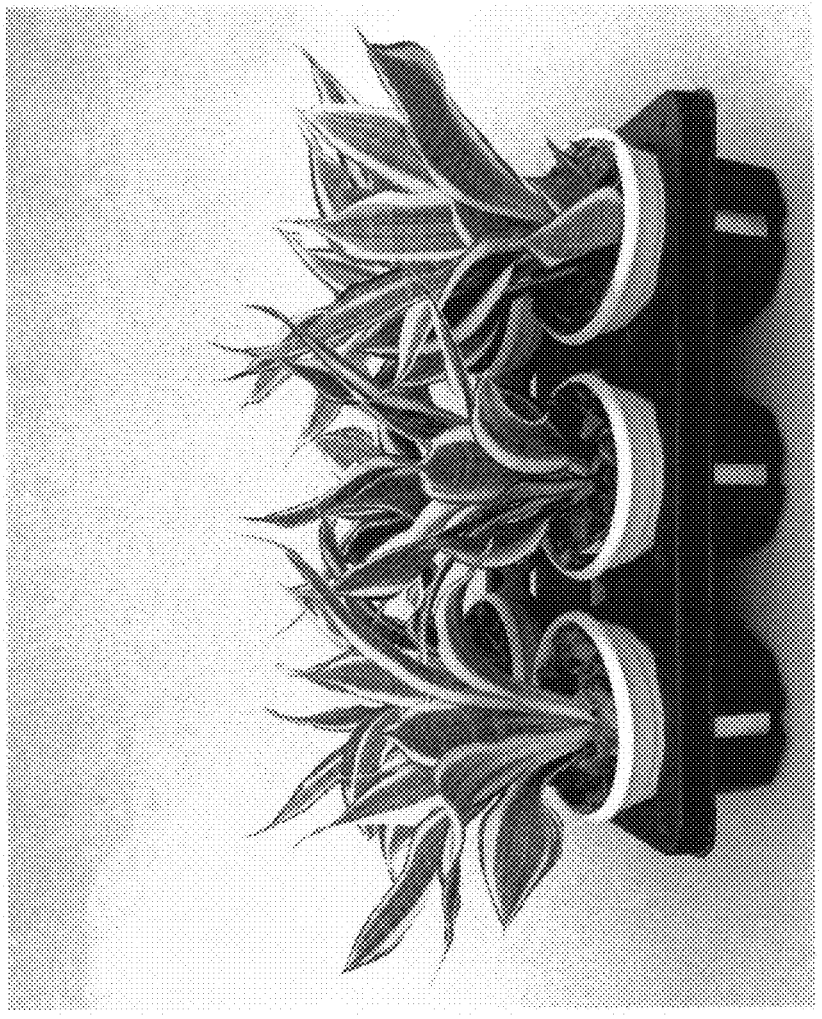

FIG. 4 illustrates a side view of 6 plants of 'HANSOTI23' grown under lower light (same growing conditions as plants in FIG. 1 and FIG. 2). Plants are approximately 2.5 to 3 months old.

Figure 5:
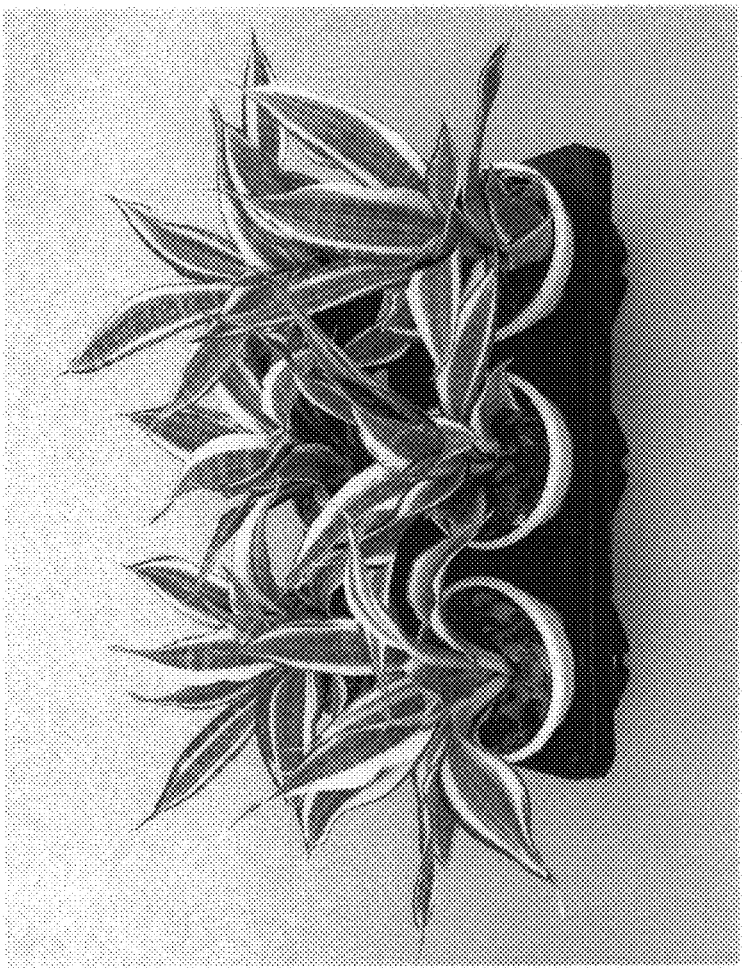

FIG. 5 illustrates the same plants as in FIG. 4 from a higher angle.

Figure 6:
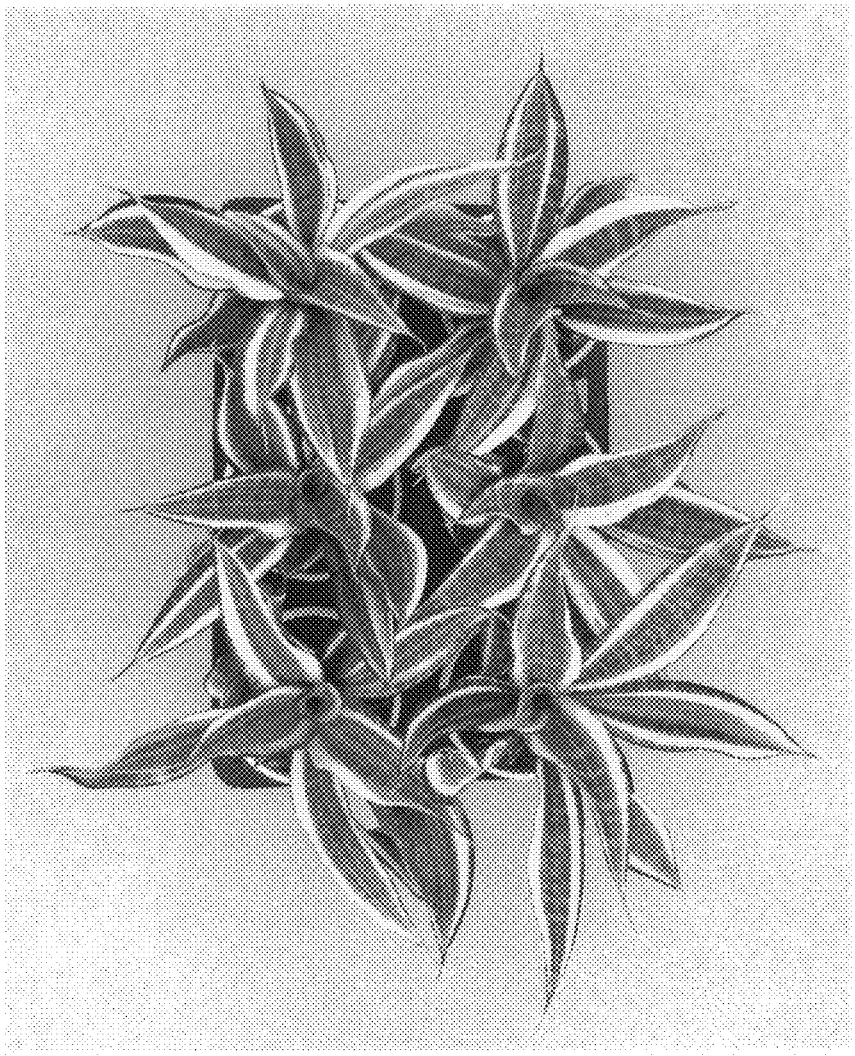

FIG. 6 illustrates the same plants as in FIG. 4 and FIG. 5 from the top view.

Figure 7:
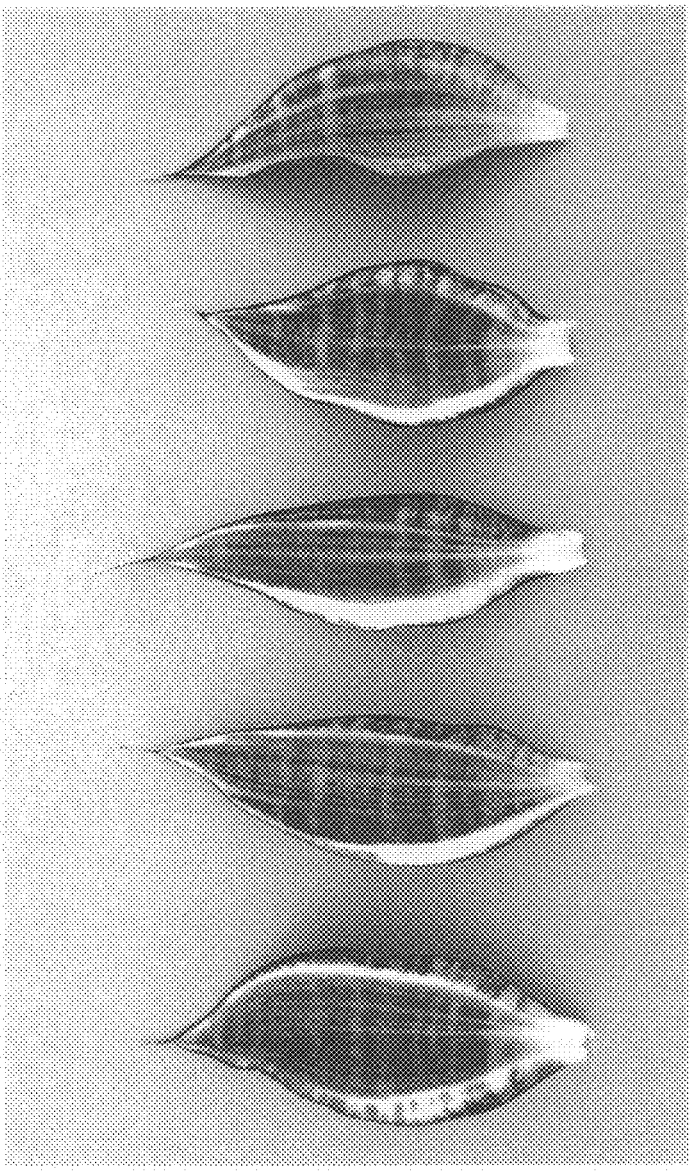

FIG. 7 illustrates individual leaves of 'HANSOTI23'.

DETAILED BOTANICAL DESCRIPTION

The new *Sansevieria* 'HANSOTI23' has not been observed under all possible environmental conditions. The phenotype of the new cultivar may vary with variations in environment such as temperature, light intensity, fertilizer levels and composition and day length without any change in the genotype of the plant.

The aforementioned photographs, together with the following observations, measurements and values describe the new *Sansevieria* cultivar 'HANSOTI23' plants grown in an open poly house (high tunnel) at Village Asle, District Satara, Maharashtra State in Western India. Average temperature in Asle is 25° C. with summer highs of 39° C. and winter lows of 6° C. Plants grow under natural light conditions and between 30% to 75% shade levels depending on the season (higher shade in hot summer conditions).

This crop gets nearly constant fertilization to increase production, Constant Liquid Feed at approximately 150 ppm N, 30 ppm P and 150 ppm K is used along with micronutrients. Production is closely related with proper and complete plant nutrition and an open soilless growing media based on coconut coir. The plants are grown in plastic pots on metal benching in spacing trays.

Color references are made to The Royal Horticultural Society Colour Chart (R.H.S.), (April 2009) except where general colors of ordinary significance are used.

The photographs and descriptions were taken during the Winter season in Asle, District Satara, Maharashtra State, India when outdoor day temperature was 25° C. to 30° C. The age of the plants described is 3 to 4 months.

Botanical classification: *Sansevieria trifasciata* 'HANSOTI23'.

General information:

*Parentage.*—*Sansevieria trifasciata* 'Midi Green' (unpatented).

*Optimal growth conditions.*—

*Light intensities.*—High adaptability to outdoor or indoor conditions.

*Temperature.*—Day: 25° C. to 35° C. Night: 12° C. to 25° C.

*Temperature tolerance.*—Tolerant to a low temperature of about 8° C. and a high temperature of 38° C. and above, very heat tolerant.

*Fertilization.*—Constant feed of 150 ppm N, 30 ppm P and 150 ppm K is used along with micronutrients with occasional leaching.

*Growth regulators.*—Not necessary for growth, however rooting hormone aids in rapid and prolific rooting of offsets.

Propagation:

*Typical.*—Side suckers which come true to type.

*Rooting habit and description.*—Rhizomes are elongated, fleshy, giving rise to offsets (side shoots). Offsets root easily with fibrous adventitious roots from cut end. Colored cream to brown, not accurately measured with R.H.S. chart.

*Time to initiate roots.*—15 to 20 days at 25 to 30° C.

*Time to produce a rooted liner.*—About 45 days at 25° C. to 30° C.

*Time to produce a sales ready* 12 *cm potted plant from liner.*—About 3 months at 25° C. to 30° C.

Plant:

*General appearance and form.*—Upright rosette.

*Height.*—About 20 to 30 cm when grown in 12 cm pots.

*Spread.*—About 25 to 30 cm when grown when grown in a 12 cm size container.

*Form.*—Monocot; leaf bases arranged in a rosette around growth point.

*Shape.*—Inverted triangle.

*Growth rate.*—Moderate to rapid.

Foliage:

*Quantity.*—About 7 to 9 in a 12 cm, ready to sell plant. Increases with age.

*Arrangement and attachment.*—Single, leaf bases arranged stiffly in a rosette around a central growth point.

*Leaf length.*—About 20 to 30 cm, full mature leaf.

*Leaf width.*—About 6 cm, full mature leaf.

*Overall shape of leaf.*—Lanceolate.

*Aspect.*—Slightly to moderately undulate.

*Apex shape.*—Acute, aristate soft tip.

*Base shape.*—Truncate.

*Margin.*—Entire, sharp, smooth.

*Texture.*—Upper Surface: Smooth and waxy texture.

*Texture.*—Under Surface: Smooth and waxy texture.

*Pubescence*.—None.

*Color*.—Upper surface mature leaf: Basal cream colour near 11B to 11D with dark central band varying from 136B to lighter bands near 138B or 138C. Central band covered in overlay colored near Yellow 2D. Lower surface mature leaf: Basal cream colour near 11B to 11D with dark central band varying from 136B to lighter bands near 138B or 138C. Central band covered in overlay colored near Yellow 2D. Margin coloration: Near RHS Green 136A upper and lower surfaces. Young foliage near Yellow-Green 144D.

*Venation*.—Pattern: Longitudinal/parallel leaf shape.

*Venation color*.—Indistinguishable from leaf blade.

*Leaf fragrance*.—None.

Other:

*Inflorescence description*.—Flowers not observed to date.

*Weather resistance*.—Moderately drought tolerant.

*Pest resistance*.—Reasonably resistant to pests, susceptible to root mealybugs (*Rhizoecus pritchardi*). Typical pets include *Pseudococcidae longispinus* and *Tetranychus urticae*.

*Disease resistance*.—Occasionally shows Anthracnose and leaf spots but largely disease free from clean mother stock.

*Fruit/seed production*.—No fruits/seeds detected to date.

What is claimed is:

1. A new and distinct cultivar of *Sansevieria* plant named 'HANSOTI23' as herein illustrated and described.

* * * * *